United States Patent
Pierik et al.

(10) Patent No.: US 9,688,979 B2
(45) Date of Patent: Jun. 27, 2017

(54) BIOMOLECULE DRYING PROCESS FOR LONG-TERM STORAGE

(71) Applicant: BIOCARTIS NV, Mechelen (BE)

(72) Inventors: Anke Pierik, Eindhoven (NL); Henk Van Damme, Eindhoven (NL); Martijn Van Zelst, Eindhoven (NL); Rene Bakker, Eindhoven (NL); Pieter De Bokx, Eindhoven (NL)

(73) Assignee: BIOCARTIS NV, Mechelen (BE)

( * ) Notice: Subject to any disclaimer, the term of this patent is extended or adjusted under 35 U.S.C. 154(b) by 0 days.

(21) Appl. No.: 14/895,628

(22) PCT Filed: Jun. 11, 2014

(86) PCT No.: PCT/CH2014/000079
§ 371 (c)(1),
(2) Date: Dec. 3, 2015

(87) PCT Pub. No.: WO2014/198004
PCT Pub. Date: Dec. 18, 2014

(65) Prior Publication Data
US 2016/0122744 A1    May 5, 2016

(30) Foreign Application Priority Data

Jun. 11, 2013   (EP) .................................. 13171437

(51) Int. Cl.
*F26B 5/12*     (2006.01)
*C12N 9/96*     (2006.01)

(52) U.S. Cl.
CPC ..................................... *C12N 9/96* (2013.01)

(58) Field of Classification Search
CPC ...... F26B 5/00; F26B 5/12; F26B 5/16; F26B 7/00; A23K 1/00; A23K 1/14
USPC ................................... 34/357, 469; 210/770
See application file for complete search history.

(56) References Cited

U.S. PATENT DOCUMENTS

| | | | | |
|---|---|---|---|---|
| 4,891,319 A | * | 1/1990 | Roser | A61K 35/16 424/278.1 |
| 5,098,893 A | * | 3/1992 | Franks | A61K 9/145 514/54 |
| 6,258,341 B1 | | 7/2001 | Foster et al. | 424/45 |
| 7,669,349 B1 | * | 3/2010 | Palmer | F26B 11/16 210/770 |
| 8,263,192 B2 | * | 9/2012 | Koberstein | A61L 27/34 427/2.13 |
| 8,278,040 B2 | * | 10/2012 | Abbott | C09K 19/52 349/1 |
| 2009/0325263 A1 | * | 12/2009 | Ponaka | C12N 1/04 435/178 |
| 2010/0159529 A1 | | 6/2010 | Metzler et al. | 435/91.2 |
| 2012/0148556 A1 | * | 6/2012 | LeBowitz | A61K 9/0019 424/94.3 |
| 2016/0122744 A1 | * | 5/2016 | Pierik | C12N 9/96 34/357 |
| 2016/0287741 A1 | * | 10/2016 | Harris | A61K 33/38 |
| 2016/0317647 A1 | * | 11/2016 | Ciaramella | A61K 39/00 |

FOREIGN PATENT DOCUMENTS

| | | | | |
|---|---|---|---|---|
| EP | 0383569 | | 2/1990 | ............. C12N 11/00 |
| WO | WO 87/00196 | | 1/1957 | ............. C12N 9/96 |
| WO | WO 2008/036544 | | 3/2008 | ............. A61K 9/14 |
| WO | WO 2010/148253 | | 12/2010 | ............. A61K 38/16 |
| WO | WO 2014198004 A1 | * | 12/2014 | ............. C12N 9/96 |

OTHER PUBLICATIONS

Polysaccharide internet search using google.com on Jan. 13, 2017.*
International Search Report from corresponding International Patent Application No. PCT/CH2014/000079, dated Jul. 14, 2014.

* cited by examiner

Primary Examiner — Stephen M Gravini
(74) Attorney, Agent, or Firm — Kusner & Jaffe

(57) ABSTRACT

The present invention relates to a method for producing a storable dry composition of biomolecule. First a composition is dispensed on a surface. The composition comprises at least a biomolecule, at least a liquid volatile component, at least a polysaccharide being designed for forming together with the at least a biomolecule and a part of the at least a liquid volatile component a matrix displaying a glass transition temperature Tg. Secondly, at least a part of the liquid volatile component is evaporated by adjusting the temperature of said composition to allow the formation of the matrix. Said evaporation step is initiated at an initial temperature T1, and finished up at a final temperature T2, said final temperature T2 being above said initial temperature T1.

18 Claims, No Drawings

BIOMOLECULE DRYING PROCESS FOR LONG-TERM STORAGE

FIELD OF THE INVENTION

The present invention relates to the field of dry composition of biomolecule to enhance their long-term storage capabilities.

BACKGROUND OF THE INVENTION

Few biomolecules involved in biological reaction such as PCR or enzymatic catalysis are stable in solubilized form. Stored in solution, such biomolecules are prone to degradation reactions that turn them into forms unsuitable for any biological reaction. Therefore, those liquid sensitive biomolecules have to be dried for long-term storage to prevent their degradation in solution.

However, during the drying of a solution comprising a biomolecule among other components, the non-volatile component can have a dramatic impact on the stability of the biomolecule. Indeed, components such as inorganic salts, that are present in very small concentrations in the initial solution, can have a huge destabilizing effect as their concentrations increase while the removal of the volatile component.

Besides, the method used to dry the solution is critical as well regarding the activity of the biomolecule. At high temperatures, an enzyme can lose its activity due to denaturation or degradation.

To reach the dryness state required for long term stability, the liquid component from the composition can be removed by drying it for a long time (e.g. 16 hrs) under low pressure (e.g. 200 mBar) as mentioned in US2010/0159529. Although this process is efficient for batch scale production, it remains difficult to apply to a manufacture line for large scale production.

Another used method for fast drying consists in exposing the composition for a shorter time to high temperatures. However, exposing the composition directly to hot air may lead to undesired degradation of the biomolecule. The present invention aims to remedy all or part of the disadvantages mentioned above.

SUMMARY OF THE INVENTION

The present invention fulfils these objectives by providing a method for producing a storable dry composition of one or more biomolecules that prevents degradation of said one or more biomolecules. The present invention describes a method for producing a storable dry composition of biomolecule, comprising the successive steps of:
a. Dispensing at least a composition on a surface, the composition comprising:
   i. at least a biomolecule,
   ii. at least a liquid volatile component,
   iii. at least a polysaccharide being designed for forming together with the at least a biomolecule and a part of the at least a liquid volatile component a matrix displaying a glass transition temperature Tg,
b. Evaporating at least a part of the at least a liquid volatile component by adjusting the temperature of said composition to allow the formation of the matrix, characterized in that step b) is initiated at an initial temperature T1, and finished up at a final temperature T2, said final temperature T2 being above said initial temperature T1.

Thus, the present invention solves the above mentioned problems by initiating the drying process at an initial temperature T1, and finishing the drying process at a final temperature T2. The purpose of the initial temperature T1 is to remove as quickly as possible a large part of the liquid volatile component while the temperature is relatively low to minimize degradation of the biomolecule. Removing part of the liquid volatile component increases the viscosity of the composition. Thereby, the mobility of the biomolecule is considerably reduced which minimized the rate of degradation of biomolecule. A higher final temperature T2 permits to remove as much as possible of the remaining liquid volatile component from the composition to end up in a glassy state in which lower residual liquid volatile component content is present. Since the mobility of the biomolecule is already reduced during heating at the initial temperature T1, the impact of a higher temperature on the reactivity of the biomolecule is expected to be less important.

The term "polysaccharide" will be used in the context of this invention as polymeric carbohydrate molecule composed of 2 to 15 monosaccharide units, preferably 2 to 10 units.

According to an embodiment, the initial temperature T1 and final temperature T2 are above the glass transition temperature Tg. Thus, during the process, the matrix remains in a liquid form that permits a homogenous distribution and an optimized evaporation of at least part of the liquid volatile component.

In an embodiment, the difference between the initial temperature T1 and the glass transition temperature Tg and the difference between the final temperature T2 and the glass transition temperature Tg remain constant and positive. The glass transition temperature Tg varies depending on the fraction of the liquid volatile solvent remaining in the composition.

In an embodiment, the initial temperature T1 is maintained between about 30° C. and about 50° C. during 30 minutes, and the final temperature T2 is maintained between about 60° C. and about 90° C. during 30 minutes.

According to an embodiment, step b) is performed until the fraction of liquid volatile component of the composition reaches about 3%, preferably 2%. The biomolecule remains in an active and stabilized dry form, in a composition designed for being stored for long-term period. Thus, liquid sensitive biomolecules are less prone to degradation.

In an embodiment of the present invention, step b) is performed at initial temperature T1 until the fraction of liquid volatile component of the composition reaches about 10%. Hence, when the fraction of the liquid volatile component reached about 10%, the composition presents a viscosity that considerably reduced the mobility of the biomolecule. Then, the composition is ready to be dried at final temperature T2.

According to an embodiment, the initial temperature T1 is below 40° C.

In an embodiment, the final temperature T2 is above 80° C.

According to an embodiment, step b) further makes use of a gas flow. Evaporation of the liquid volatile component during the drying process according to the present invention decreases the vapour pressure above the composition. Thus, the gas flow contributes to the drying process.

In an embodiment, the liquid volatile component is chosen among water or alcohol, or a mixture thereof. Such liquid volatile components or mixture of thereof exhibit characteristics that are suitable for the method according the present invention. Indeed, biomolecules are generally soluble in solvent comprising water and/or alcohol. Besides, such liquid volatile components are easily evaporated via the method according to the present invention.

According to an embodiment, the biomolecule is an enzyme for amplification reaction of nucleic acid (PCR). Such biomolecules are known to be instable in solution. In an embodiment, the composition according to the present invention comprises a stabilizing agent for stabilizing a PCR reaction.

In an embodiment, the composition comprises at least 0.1 M to 0.6 M of trehalose, preferably 0.15 M to 0.3 M.

According to an embodiment, the composition comprises at least 4.0 ug/uL to 8.0 ug/ul of Bovine Serum Albumin, preferably 5.5 ug/uL to 6.5 ug/ul.

In an embodiment of the present invention, the composition comprises at least 1.0% to 30.0% of glycerol, preferably 5.0% to 15.0%.

In an embodiment, Raman spectroscopy can be used in a method according to the present invention to adapt the temperature of the composition.

In one embodiment, the method for producing a storable dry composition of biomolecule comprises the successive steps of:
 a. Dispensing at least a composition on a surface, the composition comprising:
  i. at least a biomolecule,
  ii. at least a polymer being designed for forming at least part of a matrix displaying a glass transition temperature Tg,
  iii. at least a liquid volatile component,
 b. Evaporating at least a part of the liquid volatile component by adjusting the temperature of said composition to allow the polymer to form the matrix encompassing the biomolecule,
 characterized in that step b) is initiated at an initial temperature T1, and finished up at a final temperature T2, said final temperature T2 being above said initial temperature T1.

DETAILED DESCRIPTION OF THE INVENTION

The present invention is further illustrated by the following detailed description which represents an exemplary and explanatory embodiment of a method for producing a storable dry composition of biomolecule.

A method for producing a storable dry composition of biomolecule according to the present invention comprises two steps:
 first, a step of dispensing a composition to be dried on a surface,
 Then a drying step for drying the composition between two temperatures.

The composition according to the present invention comprises at least a biomolecule. Biomolecules according to the present invention share the feature of being fragile and thus vulnerable in solution. Such biomolecules require extreme dryness condition for long term storage to prevent their degradation. In the present embodiment, the biomolecule is a PCR enzyme.

The composition according to the present invention further comprises at least a polysaccharide designed for forming together with the at least a biomolecule and a part of the at least a liquid volatile component a matrix displaying a glass transition temperature Tg. In the present case, the composition comprises trehalose in solution at 0.2 M as said polysaccharide.

Moreover, the composition according to the present invention further comprises at least a liquid volatile component for dissolving the biomolecule and the polysaccharide, the liquid volatile component being designed for being evaporated. In the present embodiment, the liquid volatile component is water.

The composition according to the present invention can advantageously comprise other reagents adapted for the intended use of the biomolecule of the composition. For example, when the biomolecule is a PCR enzyme, the composition can include primers or nucleotides or salt that are needed to achieve the PCR amplification reaction. Advantageously, bovine serum albumin at 6.25 pg/pl is incorporated in the composition in order to stabilize the amplification PCR reaction. Besides, the composition comprises 1 to 2% glycerol that is present in the commercial solution of the PCR enzyme that is being used in the reaction.

The first step of the method according to the present invention consists in dispensing the composition described above on a surface. For example, the composition is dispensed with a nozzle to produce a spot. In the described embodiment, the surface is a foil that is part of a PCR reaction chamber of an IVD apparatus.

Once the composition is dispensed on the surface, a method according to the present invention implies a drying step. The method according to the present invention comprises the step of evaporating at least a part of the liquid volatile component by adjusting the temperature of said composition to allow the formation of the matrix. This step is initiated at an initial temperature T1, and finished up at a final temperature T2, said final temperature T2 being above said initial temperature T1.

In the present embodiment, the composition is maintained at the temperature Ti of about 40° C. during 30 minutes. In another embodiment, this step could be performed until the fraction of liquid volatile component of the composition reaches about 10%. The goal is to reduce the fraction of liquid volatile component to reduce the mobility of the biomolecule which is thereby less prone to degradation. Then, the temperature is increased to a final temperature T2 to dry the composition for a determined time. In the present case, the composition is maintained at the temperature T2 of about 80° C. during 30 minutes. In another embodiment, the final temperature T2 is maintained until the fraction of liquid volatile component of the composition reaches about 2%.

In another embodiment, the final temperature T2 is reached by increasing the temperature gradually and continuously from the initial temperature T1.

Practically, the surface comprising the composition is inserted in a drying tunnel and an air flow is circulated across the tunnel and above the surface to help drying by removing the vapours of the liquid volatile component.

Advantageously, the initial temperature T1 and the final temperature T2 are chosen depending on the glass transition Tg. In the present case, the initial temperature T1 and final temperature T2 are above the glass transition temperature Tg. Moreover, the difference between the initial temperature T1 and the glass transition temperature Tg and the difference between the final temperature T2 and the glass transition temperature Tg are maintained constant and positive.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Having described the invention, the following is claimed:

1. A method for producing a storable dry composition of biomolecule, comprising:
   (a) Dispensing at least a composition on a surface, the composition comprising:
      (i) at least a biomolecule,
      (ii) at least a liquid volatile component,
      (iii) at least a polysaccharide being designed for forming together with the at least a biomolecule and a part of the at least a liquid volatile component a matrix displaying a glass transition temperature Tg,
   (b) Evaporating at least a part of the at least a liquid volatile component by adjusting a temperature of said composition to allow formation of the matrix, wherein step (b) is initiated at an initial temperature T1, and finished up at a final temperature T2, said final temperature T2 being above said initial temperature T1.

2. A method according to claim 1, wherein the initial temperature T1 and final temperature T2 are above the glass transition temperature Tg.

3. A method according to claim 1, wherein a difference between the initial temperature T1 and the glass transition temperature Tg and a difference between the final temperature T2 and the glass transition temperature Tg remain constant and positive.

4. A method according to claim 1, wherein the initial temperature T1 is maintained between about 30° C. and about 50° C. during 30 minutes, and the final temperature T2 is maintained between about 60° C. and about 90° C. during 30 minutes.

5. A method according to claim 1, wherein step (b) is performed until a fraction of liquid volatile component of the composition reaches about 3%.

6. A method according to claim 1, wherein step (b) is performed at initial temperature T1 until a fraction of liquid volatile component of the composition reaches about 10%.

7. A method according to claim 1, wherein the initial temperature T1 is below 40° C.

8. A method according to claim 1, wherein the final temperature T2 is above 80° C.

9. A method according to claim 1, wherein step (b) further makes use of a gas flow.

10. A method according to claim 1, wherein the liquid volatile component is selected from a group comprising: water, alcohol, or a mixture thereof.

11. A method according to claim 1, wherein the biomolecule is an enzyme for amplification reaction of nucleic acid.

12. A method according to claim 1, wherein the composition comprises at least 0.1 M to 0.6 M of trehalose.

13. A method according to claim 1, wherein the composition comprises at least 4.0 ug/uL to 8.0 ug/ul of Bovine Serum Albumin.

14. A method according to claim 1, wherein the composition comprises at least 1.0% to 30.0% of glycerol.

15. A method according to claim 1, wherein step (b) is performed until a fraction of liquid volatile component of the composition reaches about 2%.

16. A method according to claim 1, wherein the composition comprises at least 0.15 M to 0.3 M of trehalose.

17. A method according to claim 1, wherein the composition comprises at least 5.5 ug/uL to 6.5 ug/ul of Bovine Serum Albumin.

18. A method according to claim 1, wherein the composition comprises at least 5.0% to 15.0% of glycerol.

* * * * *